United States Patent [19]

Phillips

[11] 3,948,973

[45] Apr. 6, 1976

[54] HALOCYCLOPROPYL SUBSTITUTED PHENOXYALKANOIC ACIDS

[75] Inventor: Donald K. Phillips, East Greenbush, N.Y.

[73] Assignee: Sterling Drug Inc., New York, N.Y.

[22] Filed: Feb. 19, 1974

[21] Appl. No.: 443,418

Related U.S. Application Data

[63] Continuation-in-part of Ser. No. 284,577, Aug. 29, 1972, abandoned.

[30] Foreign Application Priority Data

Aug. 13, 1973 United Kingdom............... 38311/73

[52] U.S. Cl....... 260/473 G; 260/465 F; 260/473 F; 260/501.1; 260/501.17; 260/612 R; 260/578; 260/612 D; 260/619 D; 260/621 R; 424/308; 424/316; 424/317; 260/520 C
[51] Int. Cl.²......................................... C07C 69/76
[58] Field of Search............. 260/520, 473 G, 473 F

[56] References Cited
UNITED STATES PATENTS

| 3,362,997 | 1/1968 | Bolhofer | 260/473 G |
| 3,363,003 | 1/1968 | Bolhofer | 260/520 |
| 3,383,411 | 5/1968 | Schultz et al. | 260/520 |
| 3,598,860 | 8/1971 | Griot | 260/473 G |
| 3,598,862 | 8/1971 | Griot | 260/473 G |
| 3,694,512 | 9/1972 | Narayanan | 260/473 F |
| 3,839,431 | 10/1974 | Sheehan | 260/520 |

OTHER PUBLICATIONS

Burger, "Medicinal Chemistry," Wiley–Interscience, N.Y., (1970), pp. 71, 72.

Primary Examiner— Terapane
Attorney, Agent, or Firm—Thomas L. Johnson; B. Woodrow Wyatt

[57] ABSTRACT

Halocyclopropyl substituted phenoxyalkanoic acids and esters thereof, having hypocholesteremic activity are prepared via several alternative synthetic approaches, involving as the key reactions interaction of a substituted phenylalkene with a carbene source to introduce the halocyclopropyl moiety, and reaction of a substituted phenol with chloroform and a lower-alkanone in the presence of base, or with a lower-alkyl α-bromo-alkanoate, to form the phenoxyalkanoic acid moiety.

11 Claims, No Drawings

HALOCYCLOPROPYL SUBSTITUTED PHENOXYALKANOIC ACIDS

This application is a continuation-in-part of my copending application Ser. No. 284,577, filed Aug. 29, 1972 now abandoned.

This invention relates to novel aryloxy aliphatic acids and alky esters thereof, to methods for the preparation thereof, and certain novel intermediates. In particular the invention is concerned with halocyclopropyl-substituted phenoxyalkanoic acids and lower-alkyl esters thereof.

The compounds of the invention have the following general formula:

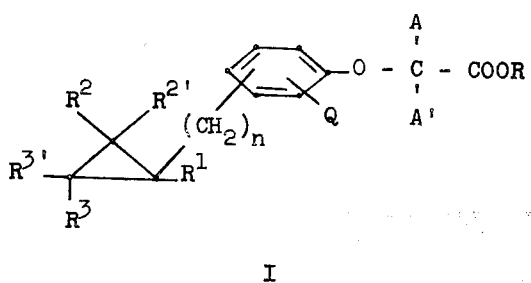

I wherein:
R is hydrogen or alkyl of 1–6 carbon atoms;
A and A' are alkyl of 1–3 carbon atoms;
Q is hydrogen, halogen or alkyl of 1–3 carbon atoms;
$R^1$ is hydrogen, alkyl of 1–3 carbon atoms or phenyl;
$R^2$ is hydrogen or halogen;
$R^{2'}$ is hydrogen or halogen, at least one of $R^2$ and $R^{2'}$ being halogen;
$R^3$ is hydrogen, alkyl of 1–3 carbon atoms or phenyl;
$R^{3'}$ is hydrogen or alkyl of 1–3 carbon atoms;
n is 0 or 1;
or a compound of the above formula where Q and $R^3$ together form an ethylene bridge and $(CH_2)_n$ is a single bond (n is 0) to the benzene ring ortho to Q, thereby forming a six-membered non-aromatic carbocyclic ring of a 2,3-dihydro-1H-cyclopropa[a]naphthalene ring system. Also contemplated are the pharmacologically acceptable salts of the compounds of the above formula where R is hydrogen.

In the foregoing definitions, the alkyl groups can be straight or branched, and halogen stands for any of the four halogens, fluorine, chlorine, bromine and iodine.

Preferred pharmacologically acceptable salts include the sodium, calcium, magnesium and ammonium salts, and salts of organic amines of low toxicity, for example, the diethanolamine and N-methylglucamine salts.

The compounds of the invention are prepared by means of a process step which comprises treating a compound of Formula II, IIa, IIb or IIc with a medium generating a carbene: $CR^2R^{2'}$, or treating a compound of the Formula IId with a medium generating a carbene: $CR^3R^{3'}$.

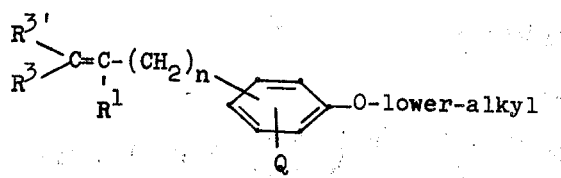

II

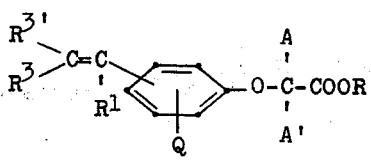

IIa

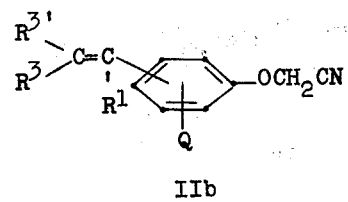

IIb

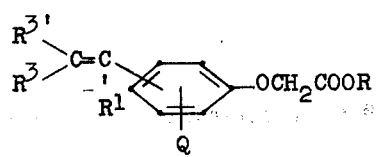

IIc

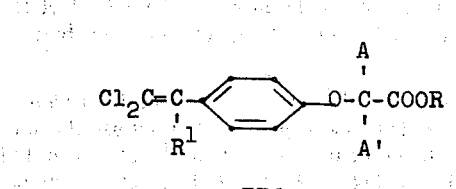

IId

In the foregoing formulas, R is lower-alkyl, and $R^1$, $R^2$, $R^{2'}$, $R^3$, $R^{3'}$, Q, A, A' and n have the meanings given above.

The carbene reaction process described above can be used in a number of alternative synthetic approaches to the compounds of Formula I as illustrated by the following reaction sequences:

METHOD A

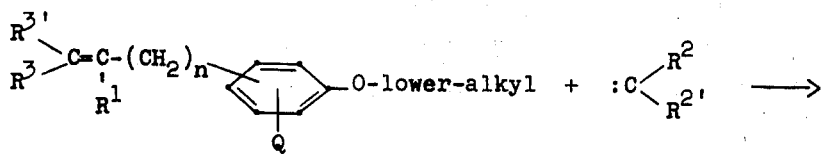

II

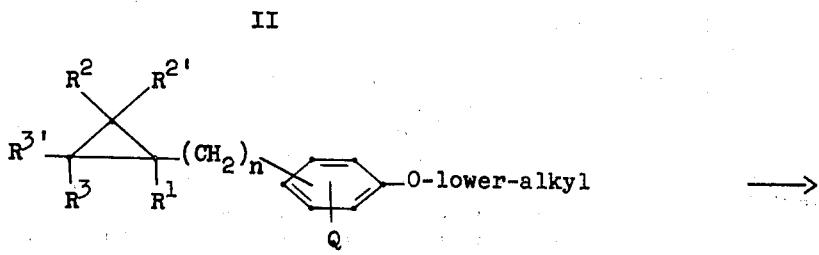

III

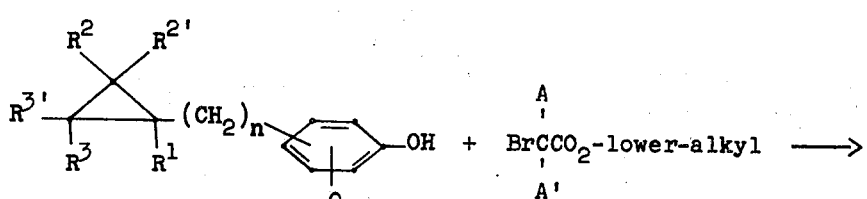

IV

I (R is lower-alkyl) ⟶ I (R is H)

In Method A above an alkenyl substituted phenol lower-alkyl ether of formula II (where $R^1$, $R^3$, $R^{3'}$ and Q have the meanings given hereinabove, and lower-alkyl has from one to four carbon atoms) is caused to react with a medium generating a carbene, $:CR^2R^{2'}$ (where $R^2$ and $R^{2'}$ have the meanings given hereinabove).

The carbenes, $:CR^2R^{2'}$, can be generated from a variety of halogenated organic compounds. Particularly useful media for this purpose are haloforms in the presence of a strong base such as potassium tertiary-butoxide. The haloforms thus used include chloroform (producing $:CCl_2$), bromoform ($:CBr_2$), iodoform ($:CI_2$), chlorodifluoromethane ($:CF_2$), and the like. Other souces of carbenes include chlorodiazomethane ($:CHCl$), $FCl_2CCOCCl_2F$ ($:CFCl$), ethyl trichloroacetate ($:CCl_2$), phenyl (trichloromethyl)mercury ($:CCl_2$), phenyl (bromodichloromethyl)mercury ($:CBr_2$), sodium chlorodifluoroacetate ($:CF_2$), sodium trichloroacetate ($:CCL_2$), bis(tribromomethyl)mercury ($:CBr_2$), bromotrifluoromethane ($:CF_2$), methyl dichlorofluoroacetate ($:CFCl$), and $(CH_3)_3SnCF_3$ ($:CF_2$). The reaction generally takes place under anhydrous conditions at ambient temperature or lower.

The second step of Method A is the cleavage of the cyclopropyl-substituted phenol ether III, produced by the foregoing carbene reaction. The ether cleavage is carried out in the presence of a strong acid. The strong acid can be protonic acid, such as hydrobromic acid or hydriodic acid, or a Lewis acid such as boron tribromide. Examples of reagents for cleavage of phenol ethers include boron tribromide, boron trichloride, boron trifluoride-etherate (in presence of acetic anhydride and lithium bromide), aluminum bromide, aluminum chloride, hydriodic acid (in presence of phosphorus and acetic anhydride), hydrobromic acid, diborane and pyridine hydrochloride.

The product of the ether cleavage, the cyclopropyl substituted phenol of Formula IV, is then either treated with a bromo ester $(A)(A')C(Br)CO_2$-lower-alkyl (where A and A' have the meanings given hereinabove, and lower-alkyl has from one to six carbon atoms) in the presence of a base; or with a mixture of chloroform, a ketone of formula A-CO-A' (where A and A' have the meanings given hereinabove) and an alkali metal hydroxide. The former reaction produces a compound of Formula I where R is lower-alkyl and is carried out at a temperature between about 50° and 150°C. in the presence of a basic substance such as potassium carbonate. The latter reaction, carried out at a temperature of between about 50° and 100°C., conveniently at reflux temperature, produces a compound of Formula I where R is hydrogen. If desired, the compound of Formula I where R is lower-alkyl can be hydrolyzed by conventional procedures, as with mild alkali, to produce the compound where R is hydrogen.

When Q and R³ together form an ethylene bridge and $(CH_2)_n$ is a single bond to the benzene ring ortho to Q, the starting material in Method A is a dihydronaphthalene lower-alkyl ether of the formula

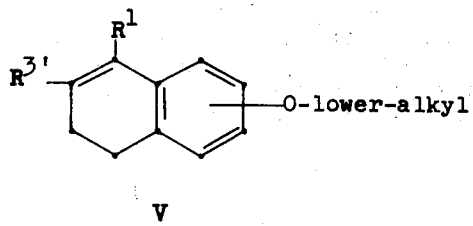

V $R^1$ and $R^{3'}$ having the meanings given hereinabove, which when treated with a medium generating a carbene $:CR^2R^{2'}$ yields a compound of the formula

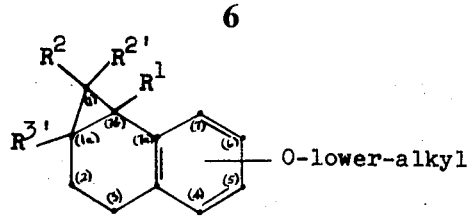

VI having the 2,3-dihydro-1H-cyclopropa[a]naphthalene ring system with numbering as indicated (Revised Ring Index No. 2119). The ether linkage of the latter is then cleaved and the resulting phenolic compound (VIa) treated either with a bromo ester $(A)(A')C(Br)-CO_2R$, or with a mixture of chloroform, a ketone A-CO-A' and an alkali metal hydroxide to produce a compound of Formula I where Q and R³ are joined to form the six-membered non-aromatic ring of a 2,3-dihydro-1H-cyclopropa[a]naphthalene ring system, viz.:

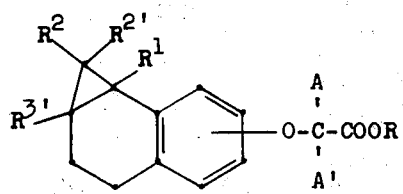

1) $CHCl_3$, A-CO-A', OH⁻
2) ROH (H⁺)
⟶

METHOD B

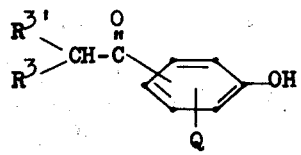

VII

↓ BrC-COOR with A, A'

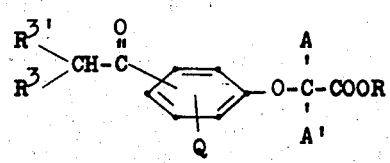

VIII (R is lower-alkyl)

$MBH_4$, $R^1Mg$-halide or $R^1$-Li
⟶

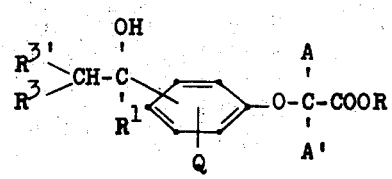

IX (R is lower-alkyl)

$-H_2O$
⟶

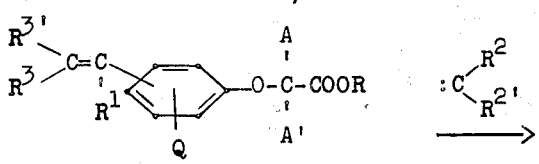

IIa (R is lower-alkyl)

I (R is lower-alkyl)

In Method B, an alkanoyl-substituted phenol of Formula VII ($R^3$, $R^{3'}$ and Q having the meanings given hereinabove) is treated either with a bromo ester (A)-(A')C(Br)-CO$_2$R (A and A' having the meanings given hereinabove and R being lower-alkyl of 1–6 carbon atoms) in the presence of a base; or with a mixture of chloroform, a ketone A-CO-A' and an alkali metal hydroxide, followed by esterification of the resulting compound of Formula VIII where R is hydrogen with a lower-alkanol. There is thus obtained a compound of Formula VIII where R is lower-alkyl.

The next step of Method B comprises treating the alkanoyl substituted phenoxyalkanoic ester of Formula VIII with an alkali metal borohydride, $R^1$-magnesium halide or $R^1$-lithium, $R^1$ being alkyl of 1–3 carbon atoms or phenyl. The reaction takes place in an inert solvent at ambient temperature or below. The reaction with alkali metal borohydride (MBH$_4$, where M is alkali metal, preferably lithium or sodium) provides a carbinol of Formula IX where $R^1$ is hydrogen and R is lower-alkyl. The reaction with $R^1$-magnesium halide or $R^1$-lithium provides a carbinol of Formula IX where $R^1$ is lower-alkyl or phenyl and R is lower-alkyl.

The carbinol of Formula IX is then dehydrated to produce an alkenyl substituted phenoxyalkanoic acid ester of formula IIa. The dehydration is carried out by heating the carbinol in an inert solvent with a dehydrating agent such as p-toluenesulfonic acid, p-toluenesulfonyl chloride, naphthalene-β-sulfonic acid, methanesulfonyl chloride-sulfur dioxide, methyl chlorosulfite, boron-trifluoride etherate, or The like. The reaction is conveniently carried out at the reflux temperature of the solvent with means for removing the water produced in the reaction.

The final step is the treatment of the olefinic ester of Formula X with a medium generating a carbene of formula :CR$^2$R$^{2'}$ (R$^2$ and R$^{2'}$ having the meanings given above), as described more fully in connection with Method A above, thereby producing a compound of Formula I where R is lower-alkyl. Method B is also applicable to preparing the dihydronaphthalene compounds of Formula I wherein Q and $R^3$ together form an ethylene bridge and (CH$_2$)$_n$ is a single bond to the benzene ring ortho to Q.

Alternatively, compounds of Formula VIII where Q is H and the substituents are para-oriented can be prepared by a Friedel-Crafts type reaction between reactants of the formulas

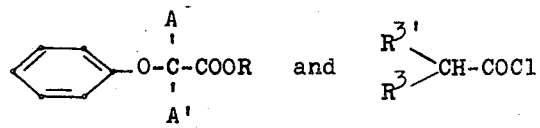

(R is lower-alkyl)

The acyl roup enters the position para to the ether linkage, and the reaction is carried out in the prresence of a Lewis acid such as aluminum chloride.

A variant on this approach involves a Friedel-Crafts reaction between a phenoxyalkanoic ester and dichloroacetyl chloride to afford a dichloroacetophenone derivative of the formula

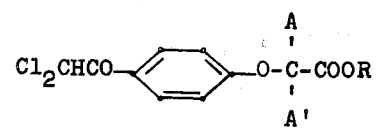

VIIIc

Following the analogous steps of Method B above, the latter can be converted to a carbinol of formula

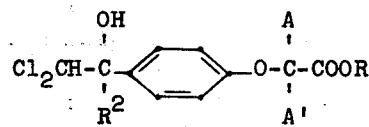

IXc and an olefin of formula

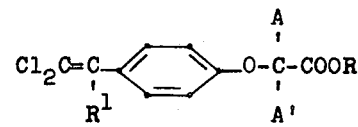

IId

Finally, the latter is treated with a medium generating unsubstituted carbene (:CH$_2$) or a substituted carbene (:CR$^3$R$^{3'}$), where $R^3$ and $R^{3'}$ have the meanings given hereinabove. Appropriate sources of such carbenes include diethylzine-methylene iodide, the Simmons-Smith reagent, e.g. zinc-copper couple (or zinc dust and cuprous halide) with methylene iodide or ethyliodo-methylzinc; and ethylidene iodide-diethylzinc. Phenylcarbene (:CHC$_6$H$_5$) can be generated by zinc reduction of benzaldehyde in an ether solution of boron trifluoride. There is thus produced a compound of the formula

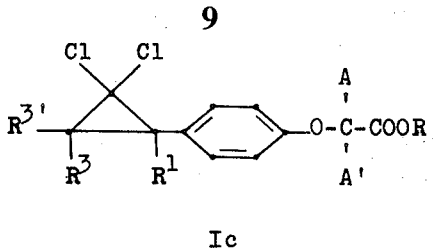

Ic by esterification of the resulting compound of Formula XII where R is hydrogen with a lower-alkanol. There is thus obtained a compound of Formula XII where R is lower-alkyl.

The next step of Method C comprises treating the alkanoyl substituted phenoxyalkanoic ester of Formula XII with a Wittig reagent, e.g., a triphenylphosphonium bromide derivative $(C_6H_5)_3$-P-CH($R^3$)$R^{3'}$ )Br ($R^3$ and

METHOD C

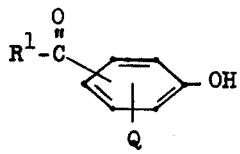

XI

1) $CHCl_3$, A-CO-A', OH$^-$
2) ROH (H$^+$)
$\longrightarrow$

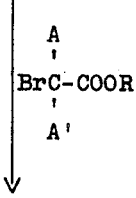

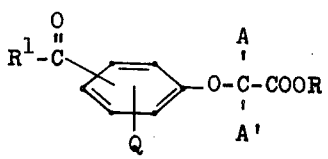

XII (R is lower-alkyl)

$(C_6H_5)_3$-P-CH($R^3$)($R^{3'}$)Br
$\longrightarrow$

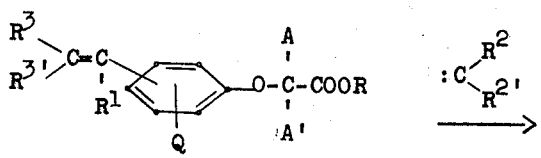

IIa (R is lower-alkyl)

$:C\begin{smallmatrix}R^2\\R^{2'}\end{smallmatrix}$

I (R is lower-alkyl)

METHOD C

In Method C, an alkanoyl-substituted phenol of Formula XI ($R^1$ having the meaning given hereinabove) is treated either with a bromo ester (A)(A')C(Br)-$CO_2$R (A and A' having the meanings given hereinabove and R being lower-alkyl of 1–6 carbon atoms) in the presence of a base; or with a mixture of chloroform, a ketone A-CO-A' and an alkali metal hydroxide, followed by esterification of the resulting compound of Formula XII where R is hydrogen with a lower-alkanol. There is thus obtained a compound of Formula XII where R is lower-alkyl.

$R^{3'}$ having the meanings given hereinabove) in the presence of a strong base such as sodium hydride, heated between about 50° and 100°C. in an inert, anhydrous solvent. There is thereby produced an alkenyl substituted phenoxyalkanoic acid ester of Formula IIa, which, as described previously under Method B can be converted by carbene reaction to a compound of Formula I where R is lower-alkyl.

METHOD D

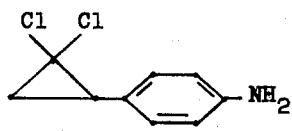

XIII

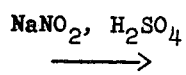

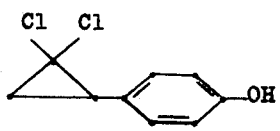

XIV

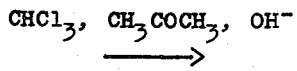

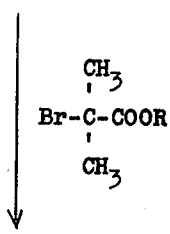

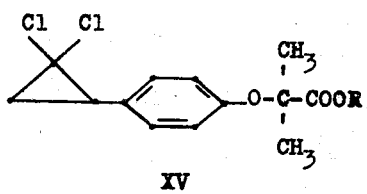

XV

METHOD D

Method D is a process modification for preparing a preferred species starting from commercially available p-(2,2-dichlorocyclopropyl)aniline (XIII). The latter is subjected to diazotization and hydrolysis to produce p-(2,2-dichlorocyclopropyl)phenol (XIV), which then is treated as described above either with a lower-alkyl 2-bromo-2methylpropionate or with a mixture of chloroform, acetone and alkali metal hydroxide, thereby producing, respectively, lower-alkyl 2-[p-(2,2-dichlorocyclopropyl)phenoxy]-2-methylpropionate (XV, R is lower-alkyl) or 2-[p-(2,2-dichlorocyclopropyl)phenoxy]-2methylpropionic acid (XV, R is hydrogen).

Alternatively, in Methods A, B, C and D, the BrC(A)(A')COOR reactant can be replaced by BrCH$_2$CN or BrCH$_2$COOR, and the alpha-alkyl residues (A=A') introduced subsequently by alkylation with an alkyl iodide (A-iodide) in the presence of a base. In the event a nitrile group is present, it can be hydrolyzed to a carboxyl group with aqueous alkali. For example, in the last step of Method A, the substitution of BrCH$_2$CN for BrC(A)(A')CO$_2$-lower-alkyl yields a compound of the formula

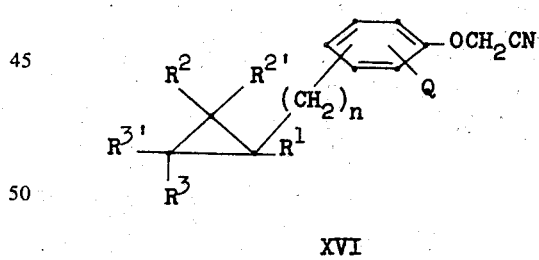

XVI which can then be alkylated with A-iodide and hydrolyzed to give a compound of Formula I. Similarly, the substitution of BrCH$_2$COOR for BrC(A)(A')CO$_2$-lower-alkyl yields a compound of the formula

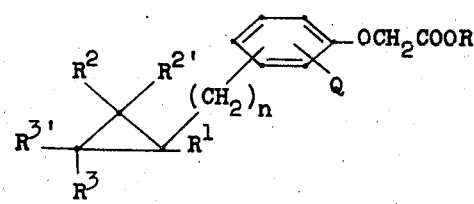

XVII which can be alkylated with A-iodide to give a compound of Formula I. Analogous transformations can be carried out on the cyclopropa[a]naphthalene intermediate VIa:

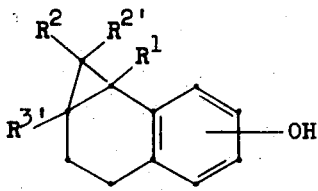

Analogous substitutions in Methods B and C affords compounds of the formula

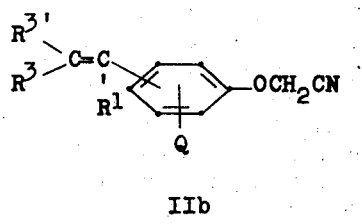

IIb and

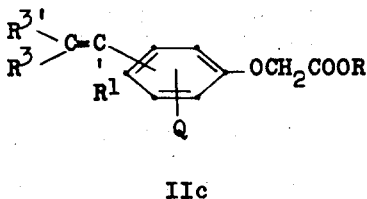

IIc

The compounds of Formulas IIb and IIc then react with a carbene :CR²R²' to give compounds of Formulas XVI and XVII.

Biological evaluation of the compounds of the invention has shown that they possess hypocholesteremic and hypotriglyceridemic activity and are therefore useful in treating atherosclerotic conditions brought about by elevated serum cholesterol and triglyceride levels.

The hypocholesteremic and hypotriglyceridemic activity was measured by oral administration to rats [Turner et al., Scand. J. Clin. Lab. Investigation 9, 210 (1949); Arnold et al., J. of Atherosclerosis Research 7, 111–115 (1967)]. Male rats are fasted for five hours, medicated via stomach tube and then fed either a normal diet or a fat diet. This regimen is continued for four days. Blood is taken by cardiac puncture on the fifth day. Serum samples are analyzed for cholesterol and triglycerides, and values are reported in mg. cholesterol or triglycerides per 100 ml. of serum. Activities of compounds are evaluated in terms of $ED_{33}$ values which are the calculated doses at which a 33 percent decrease in serum cholesterol or triglycerides occurs. The compounds of the invention were found to have $ED_{33}$ hypocholesteremic values ranging from 15 mg./kg. to 250 mg./kg. and $ED_{33}$ hypotriglyceridemic values ranging from 2 mg./kg. to 250 mg./kg. in rats maintained on normal diet. In rats maintained on a fat diet the $ED_{33}$ values were lower.

The structures of the compounds of the invention were established by the modes of synthesis, by elementary analysis and by infrared and nuclear magnetic resonance spectral determinations.

The following examples will further illustrate the invention without the latter being limited thereby.

METHOD A

EXAMPLE 1 a. p-Isopropenylanisole.

A solution of 150 g. (1.0 mole) of p-methoxyacetophenone in 1500 ml. of anhydrous ether was added dropwise over a period of 90 minutes to a solution of 22 g. (1.0 mole) of methyllithium (1.66 molar in ether) cooled in an ice bath. The reaction mixture was stirred 30 minutes at 0°C., 30 minutes at room temperature and one hour at reflux. Two additional 0.1 mole portions of methyllithium were then added to the refluxing mixture at half-hour intervals. The reaction mixture was added to aqueous ammonium chloride solution, and the water layer was separated and extracted with ether. The combined ether solutions were washed with aqueous sodium bisulfite solution, dried over anhydrous sodium sulfate and concentrated in vacuo. The residue was distilled, b.p. 75°–81°C. (1.2 mm.) to give 120.4 g. of p-isopropenylanisole.

b. p-(2,2-Dichloro-1-methylcyclopropyl)anisole.

Potassium t-butoxide (228 g., 2.04 mole) was added portionwise over a period of two and one-half hours to a stirred solution of 120 g. of p-isopropenylanisole in 750 g. of chloroform and 3500 ml. of pentane held at −40°C. The reaction mixture was stirred at −40°C. for one hour, then the cooling bath was removed and stirring was continued for three hours. The reaction mixture was quenched in ice water, the layers separated and the aqueous layer extracted with pentane. The combined pentane solutions were washed with water, dried over anhydrous sodium sulfate and concentrated in vacuo to give 190 g. of p-(2,2-dichloro-1-methylcyclopropyl)anisole as an oil.

c. p-(2,2-Dichloro-1-methylcyclopropyl)phenol.

A solution of 6.1 g. (0.0242 mole) of boron tribromide in 25 ml. of methylene dichloride was added dropwise to a stirred solution of 6.1 g. (0.0264 mole) of p-(2,2-dichloro-1-methylcyclopropyl)anisole in 25 ml. of methylene dichloride cooled in an ice bath. The reaction mixture was stirred at 0° for one hour, then the ice bath was removed and the mixture stirred for an additional one hour. The reaction mixture was quenched in ice water and the layers separated. The aqueous layer was extracted with methylene dichloride, and the combined methylene dichloride solutions were washed with water and with dilute sodium hydroxide solution. At this point the sodium salt of p-(2,2-dichloro-1-methylcyclopropyl)phenol separated and was collected by filtration. The filter cake was combined with the original aqueous layer and acidified with concentrated hydrochloric acid. The acidified solution was extracted with ether and the ether dried over anhydrous sodium sulfate and concentrated in vacuo. The residue was recrystallized from carbon tetrachloride to give p-(2,2-dichloro-1-methylcyclopropyl)phenol, m.p. 125°–126°C.

d. 2-[p-(2,2-Dichloro-1-methylcyclopropyl)phenoxy]-2-methylpropionic acid

[I; A, A' and R¹ are CH₃, R, R³, R³' and Q are H, R² and R²' are Cl, and n is O; para orientation].

Chloroform (5.4 g.) was added dropwise to a mixture of 9.1 g. of p-(2,2-dichloro-1-methylcyclopropyl)phenol and 7.2 g. of sodium hydroxide in 200 ml. of acetone stirred at reflux. After the chloroform addition was completed, the mixture was heated at reflux for three hours and then cooled in an ice bath. The solid sodium salt was collected by filtration, washed with cold acetone and dissolved in water. The latter solution was acidified with concentrated hydrochloric acid, and the acidified mixture was extracted with ether, and the ether was dried over anhydrous sodium sulfate and concentrated in vacuo. The residual oil was crystallized by trituration with hexane and then recrystallized from hexane to give 8.5 g. of 2-[p-(2,2-dichloro-1-methylcyclopropyl)phenoxy]-2-methylpropionic acid as a pale cream-colored solid, m.p. 108°–111°C.

By replacing the chloroform in the foregoing preparation by a molar equivalent amount of iodoform or chlorodiazomethane there can be obtained, respectively, 2-[p- (2,2-diiodo-1-methylcyclopropyl)phenoxy]-2-methylpropionic acid [I; A, A' and $R^1$ are $CH_3$, R, $R^3$, $R^{3'}$ and Q are H, $R^2$ and $R^{2'}$ are iodine, and $n$ is O; para orientation] or 2-[p-(2-chloro-1-methylcyclopropyl)phenoxy]-2-methylpropionic acid [I; A, A' and $R^1$ are $CH_3$, R, $R^{2'}$, $R^3$, $R^{3'}$ and Q are H, $R^2$ is Cl, and $n$ is O; para orientation].

EXAMPLE 2 a. p-(2,2-Difluoro-1-methylcyclopropyl)anisole.

A warm solution of 91.5 g. of sodium chlorodifluoroacetate (previously dried at 50°C. in vacuo) in 175 ml. of diglyme was added dropwise over a period of 90 minutes to a stirred and refluxing solution of 74 g. of p-isopropenylanisole in 500 ml. of diglyme, containing a trace of trinitrobenzene and 4-t-butylpyrocatechol as stabilisers. The reaction mixture was stirred at reflux for five minutes, then cooled and filtered to remove sodium chloride. The sodium chloride was washed with a little diglyme and then with pentane, and the combined washings and the filtrate were mixed with 3 liters of water and extracted three times with pentane. The pentane solution was washed with 10% aqueous potassium hydroxide, then with water, dried over anhydrous sodium sulfate and concentrated in vacuo to give 96.5 g. of p-(2,2-difluoro-1-methylcyclopropyl)anisole as a straw-colored oil.

b. p-(2,2-Difluoro-1-methylcyclopropyl)phenol was prepared from 9.9 g. of p-(2,2-difluoro-1-methylcyclopropyl)anisole and 20 g. of boron tribromide in 200 ml. of ethylene dichloride according to the procedure described above in Example 1, part (c), affording 9 g. of pinkish oil which solidified upon standing.

c. 2-[p-(2,2-Difluoro-1-methylcyclopropyl)phenoxy]-2-methylpropionic acid [I; A, A' and $R^1$ are $CH_3$, R, $R^3$, $R^{3'}$ and Q are H, $R^2$ and $R^{2'}$ are F, and n is O; para orientation] was prepared from 9.0 g. of p-(2,2-difluoro-1-methylcyclopropyl)phenol, 10.9 g. of sodium hydroxide and 8.1 g. of chloroform in 200 ml. of acetone according to the procedure described above in Example 1, part (d). The product was recrystallized from hexane to give 8.5 g. of 2-[p-(2,2-difluoro-1-methylcyclopropyl)phenoxy]-2-methylpropionic acid as a pale cream-colored solid, m.p. 110°–111°C.

EXAMPLE 3 a. p-(2,2-Dibromo-1-methylcyclopropyl)anisole.

Potassium t-butoxide (84 g., 0.75 mole) was added portionwise over a period of two hours to a stirred mixture of 45 g. (0.3 mole) of p-isopropenylanisole and 480 g. (1.9 mole) of bromoform in 1350 ml. of pentane cooled in a dry ice bath. For the first 90 minutes the addition was carried out at −40°C., then for 30 minutes at −10°C. The reaction mixture was stirred for one hour at −10°C., then the cooling bath was removed and stirring continued for three hours. The mixture was quenched in ice water, the layers were separated and the organic layer was washed with water, dried over anhydrous sodium sulfate and concentrated in vacuo to give 99.5 g. of p-(2,2-dibromo-1-methylcyclopropyl)anisole as a red-brown oil.

b. p-(2,2-Dibromo-1-methylcyclopropyl)phenol was prepared from 10 g. of p-(2,2-dibromo-1-methylcyclopropyl)anisole, 7.5 g. of boron tribromide and 100 ml. of methylene dichloride according to the procedure described above in Example 1, part (c). There was thus obtained 6 g. of p-(2,2-dibromo-1-methylcyclopropyl)phenol as an off-white solid.

c. 2-[p-(2,2-Dibromo-1-methylcyclopropyl)phenoxy]-2-methylpropionic acid [I; A, A' and $R^1$ are $CH_3$, R, $R^3$, $R^{3'}$ and Q are H, $R^2$ and $R^{2'}$ are Br, and $n$ is 0; para orientation] was prepared from 11.7 g. of p-(2,2-dibromo-1-methylcyclopropyl)phenol, 15.2 g. of sodium hydroxide, 11.3 g. of chloroform and 250 ml. of acetone according to the procedure described above in Example 1, part (d). There was thus obtained 10.2 g. of 2- [p-(2,2-dibromo-1-methylcyclopropyl)phenoxy]-2-methylpropionic acid as a pale cream-colored solid, m.p. 130°–131.5°C. when recrystallized from an ether-hexane mixture.

EXAMPLE 4 a. p-(2,2-Dichloro-3,3-dimethylcyclopropyl)anisole was prepared from 58.3 g. of p-(2,2-dimethylvinyl)anisole, 102 g. of potassium t-butoxide, 180 ml. of chloroform and 1800 ml. of pentane according to the procedure described above in Example 1, part (b). The product was recrystallized from hexane to produce p-(2,2-dichloro-3,3-dimethylcyclopropyl)anisole in the form of colorless needles, m.p. 54.5°–57°C.

b. p-(2,2-Dichloro-3,3-dimethylcyclopropyl)phenol was prepared from 65.8 g. of p-(2,2-dichloro-3,3-dimethylcyclopropyl)anisole and 37.5 g. of boron tribromide according to the procedure described above in Example 1, part (c). There was thus obtained 23.5 g. of p-(2,2-dichloro-3,3-dimethylcyclopropyl)phenol, m.p. 111°–111.5°C. when recrystallized from a benzene-hexane mixture.

c. 2-[p-(2,2-Dichloro-3,3-dimethylcyclopropyl)phenoxy]-2-methylpropionic acid [I; A, A', $R^3$ and $R^{3'}$ are $CH_3$, R, $R^1$ and Q are H, $R^2$ and $R^{2'}$ are Cl, and n is O; para orientation] was prepared from 30.3 g. of p-(2,2-dichloro-3,3-dimethylcyclopropyl)phenol, 31.2 g. of sodium hydroxide, 23.2 g. of chloroform and 1000 ml. of acetone according to the procedure described above in Example 1, part (d). The product was obtained in the form of an oil.

EXAMPLE 5 a. p-(2,2-Difluoro-3,3-dimethylcyclopropyl)anisole was prepared from 196.6 g. of p-(2,2-dimethylvinyl)anisole and 100 g. of sodium chlorodifluoroacetate in 700 ml. of diglyme according to the procedure described above in Example 2, part (a). The product was distilled at 81°–82°C. (0.1 mm.) to give 72.0 g. of p-(2,2-difluoro-3,3-dimethylcyclopropyl)anisole.

b. p-(2,2-Difluoro-3,3-dimethylcyclopropyl)phenol was prepared from 31.8 g. of p-(2,2-difluoro-3,3-dimethylcyclopropyl)anisole and 25 g. of boron tribromide according to the procedure described above in Example 1, part (c). The product was used directly in the following reaction without further purification.

c. 2-[p-(2,2-Difluoro-3,3-dimethylcyclopropyl)phenoxy]-2-methylpropionic acid [I; A, A', R$^3$ and R$^{3'}$ are CH$_3$, R, R$^1$ and Q are H, R$^2$ and R$^{2'}$ are F, and n is O; para orientation] was prepared from 3.96 g. of p-(2,2-difluoro-3,3-dimethylcyclopropyl)phenol, 4.80 g. of sodium hydroxide, 3.58 g. of chloroform and 150 ml. of acetone according to the procedure described above in Example 1, part (d). The product was obtained in the form of an oil.

EXAMPLE 6 a. p-(1,2-Dimethylvinyl)anisole.

A mixture of 150 g. of 2-(p-methoxyphenyl)-2-butanol and 360 ml. of acetic anhydride was heated at reflux for two and one-half hours. The solvent was removed by distillation and the residue fractionally distilled. The last fraction obtained above 114°C. (10 mm.) afforded 27.0 g. of p-(1,2-dimethylvinyl)anisole, chiefly the cis isomer.

b. p-(2,2-Dichloro-1,3-dimethylcyclopropyl)anisole was prepared from 64.6 g. of p-(1,2-dimethylvinyl)anisole, 101 g. of potassium t-butoxide, 258 g. of chloroform and 1800 ml. of pentane according to the procedure described above in Example 1, part (b). The product was distilled at 90°-98°C. (0.07-0.09 mm.) to give 79.1 g. of p-(2,2-dichloro-1,3-dimethylcyclopropyl)anisole, 80% cis isomer.

c. p-(2,2-Dichloro-1,3-dimethylcyclopropyl)phenol was prepared from 79.1 g. of p-(2,2-dichloro-1,3-dimethylcyclopropyl)anisole, 46.9 g. of boron tribromide and 520 ml. of methylene dichloride according to the procedure described above in Example 1, part (c). The product was recrystallized from a benzene-hexane mixture to give 43.7 g. of p-(2,2-dichloro-1,3-dimethylcyclopropyl)phenol, cis isomer in the form of colorless needles, m.p. 79°-82°C.

d. 2-[p-(2,2-Dichloro-1,3-dimethylcyclopropyl)phenoxy]-2-methylpropionic acid [I; A, A', R$^1$ and R$^3$ are CH$_3$, R, R$^{3'}$ and Q are H, R$^2$ and R$^{2'}$ are Cl, and n is O; para orientation] was prepared from 39.1 g. of p-(2,2-dichloro-1,3-dimethylcyclopropyl)phenol, 40.6 g. of sodium hydroxide, 30.2 g. of chloroform and 1275 ml. of acetone according to the procedure described above in Example 1, part (d). The product precipitated as a sodium salt, m.p. 200°-202°C., which was acidified to the free acid and recrystallized from aqueous ethanol to give 42.5 g. of 2-[p-(2,2-dichloro-1,3-dimethylcyclopropyl)phenoxy]-2-methylpropionic acid, m.p. 133.5°-134.5°C., cis orientation of the 1- and 3-methyl groups.

EXAMPLE 7 a. o-(2,2-Dichlorocyclopropyl)anisole was prepared from 40.2 g. of o-vinylanisole, 84 g. of potassium t-butoxide and 214 g. of chloroform in 1500 ml. of pentane according to the procedure described above in Example 1, part (b). The product was distilled at 80°-85°C. (0.1 mm.) to give 7.94 g. of o-(2,2-dichlorocyclopropyl)anisole.

b. o-(2,2-Dichlorocyclopropyl)phenol was prepared from 7.8 g. of o-(2,2-dichlorocyclopropyl)anisole and 5.3 g. of boron tribromide according to the procedure described above in Example 1, part (c), affording 7.1 g. of oil used directly in the following reaction.

c. Ethyl 2-[o-(2,2-dichlorocyclopropyl)phenoxy]-2-methylpropionate [I; A and A' are CH$_3$, R is C$_2$H$_5$, R$^1$, R$^3$, R$^{3'}$ and Q are H, R$^2$ and R$^{2'}$ are Cl, and n is O; ortho orientation] was prepared from 6.6 g. of o-(2,2-dichlorocyclopropyl)phenol, 12.7 g. of ethyl α-bromoisobutyrate and 13.5 g. of anhydrous potassium carbonate in 30 ml. of dimethylformamide according to the procedure described below in Example 12, part (a). The product was distilled at 98°-100°C. (0.05 mm.) to give 4.78 g. of ethyl 2-[o-(2,2-dichlorocyclopropyl)phenoxy]-2-methylpropionate as a very pale yellow oil.

EXAMPLE 8 a. p-(2,2-Difluorocyclopropyl)anisole was prepared from 129 g. of p-vinylanisole and 170 g. of sodium chlorodifluoroacetate in 1500 ml. of diglyme according to the procedure described above in Example 2, part (a). There was thus obtained 122 g. of p-(2,2-difluorocyclopropyl)anisole as a yellow oil.

b. p-(2,2-Difluorocyclopropyl)phenol was prepared from 120 g. of p-(2,2-difluorocyclopropyl)anisole and 81 g. of boron tribromide according to the procedure described above in Example 1, part (c), affording 72 g. of oil used directly in the following reaction.

c. 2-[p-(2,2-Difluorocyclopropyl)phenoxy]-2-methylpropionic acid [I; A and A' are CH$_3$, R, R$^1$, R$^3$, R$^{3'}$ and Q are H, R$^2$ and R$^{2'}$ are F, and n is O; para orientation] was prepared from 25.5 g. of p-(2,2-difluorocyclopropyl)phenol, 36.0 g. of sodium hydroxide, 26.8 g. of chloroform and 1100 ml. of acetone according to the procedure described above in Example 1, part (d). The product was recrystallized from a benzene-hexane mixture to give 22 g. of 2-[p-(2,2-difluorocyclopropyl)phenoxy]-2-methylpropionic acid as cream-colored needles, m.p. 97°-99°C.

EXAMPLE 9 a. p-(2,2-Dichlorocyclopropylmethyl)anisole.

A mixture of 81.5 g. of p-(2-propenyl)anisole and 80.9 g. of phenyl dichlorobromomethylmercury (C$_6$H$_5$HgCCl$_2$Br) in 200 ml. of benzene was heated at reflux for five and one-half hours. The product was isolated and distilled to remove unchanged starting material and then chromatographed on 1200 g. of silica gel and eluted with pentane and with pentane containing 1-4% ether. There was thus obtained 28 g. of p-(2,2-dichlorocyclopropylmethyl)anisole as a yellow oil.

b. p-(2,2-Dichlorocyclopropylmethyl)phenol was prepared from 28 g. of p-(2,2-dichlorocyclopropylmethyl)anisole and 20 g. of boron tribromide according to the procedure described above in Example 1, part (c). The product was recrystallized from a benzene-cyclohexane mixture to give 17.3 g. of p-(2,2-dichlorocyclopropylmethyl)phenol as a beige solid, m.p. 57°-62°C.

c. Ethyl 2-[p-(2,2-dichlorocyclopropylmethyl)phenoxy]-2-methylpropionate [I; A and A' are CH$_3$, R is C$_2$H$_5$, R$^1$, R$^3$, R$^{3'}$ and Q are H, R$^2$ and R$^{2'}$ are Cl, and n is 1; para orientation] was prepared from 17.8 g. of p-(2,2-dichlorocyclopropylmethyl)phenol, 56 g. of ethyl α-bromoisobutyrate and 51.3 g. of potassium carbonate according to the procedure described below in Example 12, part (a). There was thus obtained 20.6 g. of ethyl 2-[p-(2,2-dichlorocyclopropylmethyl)phenoxy]-2-methylpropionate as a yellow oil.

d. 2-[p-(2,2-Dichlorocyclopropylmethyl)phenoxy]-

2-methylpropionic acid [I; A and A' are $CH_3$, R, $R^1$, $R^3$, $R^{3'}$ and Q are H, $R^2$ and $R^{2'}$ are Cl, and $n$ is 1; para orientation].

A mixture of 19 g. of ethyl 2-[p-(2,2-dichlorocyclopropylmethyl)phenoxy]-2-methylpropionate, 25 ml. of 10% aqueous sodium hydroxide and 25 ml. of ethanol was stirred for three hours at room temperature. The reaction mixture was acidified and the resulting product collected and recrystallized twice from hexane to give 10.0 g. of 2-[p-(2,2-dichlorocyclopropylmethyl)-phenoxy]-2-methylpropionic acid, m.p. 78°–80°C.

EXAMPLE 10 a. 1,1-Dichloro-2,3-dihydro-5-methoxy-1H-cyclopropa[a]naphthalene [VI; $R^1$ and $R^{3'}$ are H, $R^2$ and $R^{2'}$ are Cl, lower-alkyl is $CH_3$] was prepared from 48 g. of 6-methoxy-3,4-dihydronaphthalene, 84 g. of potassium t-butoxide and 227 g. of chloroform in 1350 ml. of pentane according to the procedure described above in Example 1, part (b), affording 76 g. of product as a red-brown oil.

b. 1,1-Dichloro-2,3-dihydro-1H-cyclopropa[a]-5-naphthol was prepared from 24.3 g. of 1,1-dichloro-2,3-dihydro-5-methoxy-1H-cyclopropa[a]naphthalene and 25.0 g. of boron tribromide according to the procedure described above in Example 1, part (c), affording 21.4 g. of a red-brown oil used directly in the following reaction.

c. 2-(1,1-Dichloro-2,3-dihydro-1H-cyclopropa[a]-5-naphthyloxy)-2-methylpropionic acid [I; A and A' are $CH_3$, R, $R^1$ and $R^{3'}$ are H, $R^2$ and $R^{2'}$ are Cl, Q and $R^3$ together are $CH_2CH_2$, and $n$ is 0] was prepared from 21.4 g. of 1,1-dichloro-2,3-dihydro-1H-cyclopropa[a]-5-naphthol, 22.4 g. of sodium hydroxide, 16.1 g. of chloroform and 350 ml. of acetone according to the procedure described above in Example 1, part (d). There was thus obtained 3.5 g. of 2-(1,1-dichloro-2,3-dihydro-1H-cyclopropa[a]-5-naphthyloxy)-2-methylpropionic acid as an olive-grey powder, m.p. 104°–106.5°C. when recrystallized from cyclohexane.

METHOD B

EXAMPLE 11 a. 2-(p-Propionylphenoxy)-2-methylpropionic acid was prepared from 374 g. of p-hydroxypropiophenone, 600 g. of sodium hydroxide, 390 g. of chloroform and 7 liters of acetone according to the procedure described above in Example 1, part (d). There was thus obtained 321 g. of 2-(p-propionylphenoxy)-2-methylpropionic acid.

b. Methyl 2-(p-propionylphenoxy)-2-methylpropionate.

A mixture of 118 g. of 2-(p-propionylphenoxy)-2-methylpropionic acid, 48 g. of methanol, 3.5 ml. of concentrated sulfuric acid and 150 ml. of ethylene dichloride was stirred and heated at reflux for twenty-two hours. The reaction mixture was cooled, the layers separated, and the organic layer was washed successively with water, sodium bicarbonate solution and water, and dried over anhydrous sodium sulfate and concentrated in vacuo. The residue was distilled at 122°–127°C. (0.08 mm.) to give 114.5 g. of methyl 2-(p-propionylphenoxy)-2-methylpropionate, m.p. 47°–49°C.

c. Methyl 2-[p-(1-hydroxypropyl)phenoxy]-2-methylpropionate.

Sodium borohydride (10.6 g., 0.279 mole) was added to a stirred solution of 114.5 g. (0.458 mole) of methyl 2-(p-propionylphenoxy)-2-methylpropionate in 500 ml. of methanol, held at 5°C. in an ice bath. After the exothermic reaction had slowed, the ice bath was removed and the reaction mixture stirred for one hour at room temperature. The solvent was removed in vacuo, and the residue partitioned between ether and water containing acetic acid in slight excess of that needed to make the aqueous layer acidic. The ether layer was separated, washed with sodium bicarbonate solution, dried over anhydrous sodium sulfate and concentrated in vacuo. There was thus obtained 113 g. of methyl 2-[p-(1-hydroxypropyl)phenoxy]-2-methylpropionate as a pale straw-colored oil.

d. Methyl 2-[p-(1-propenyl)phenoxy]-2-methylpropionate.

A solution of 113 g. of methyl 2-[p-(1-hydroxypropyl)phenoxy]-2-methylpropionate and 1.5 g. of p-toluenesulfonic acid in 1000 ml. of toluene was heated at reflux under a water trap for one hour. The reaction mixture was cooled, washed with aqueous sodium bicarbonate solution, dried over anhydrous sodium sulfate and concentrated in vacuo. The residue was distilled at 95°–100°C. (0.05–0.08 mm.) to give 33 g. of methyl 2-[p-(1-propenyl)phenoxy]-2-methylpropionate, $n_D^{27} = 1.5281$.

e. Methyl 2-[p-(2,2-dichloro-3-methylcyclopropyl)phenoxy]-2-methylpropionate

[I; A, A', R and $R^3$ are $CH_3$, $R^1$, $R^{3'}$ and Q are H, $R^2$ and $R^{2'}$ are Cl, and n is 0; para orientation] was prepared from 37.5 g. of methyl 2-[p-(1-propenyl)-phenoxy[-2-methylpropionate, 45 g. of potassium t-butoxide and 120 mg. of chloroform in 750 ml. of pentane according to the procedure described above in Example 1, part (b). The product was chromatographed twice on a column of 2 kg. of silica gel and the column was eluted with pentane-ether 3:1 to give 41.3 g. of methyl 2-[p-(2,2-dichloro-3-methylcyclopropyl)-phenoxy]-2-methylpropionate, $n_D^{29} = 1.5252$.

EXAMPLE 12 a. Ethyl 2-(4-acetyl-2-chlorophenoxy)-2-methylpropionate.

A solution of 204 g. (1.2 mole) of 3-chloro-4-hydroxyacetophenone, 497 g. (3.6 mole) of potassium carbonate and 1140 ml. of dimethylformamide was heated to 80°C. with stirring. Ethyl 2-bromo-2-methylpropionate (230 g.) was then added over a 5 minute period, and the reaction mixture was stirred and heated for one hour. An additional 230 g. of ethyl 2-bromo-2-methylpropionate was then added, the mixture stirred one hour, an additional 68 g. of ethyl 2-bromo-2-methylpropionate added, and the mixture finally stirred for two and one-half hours. The reaction mixture was filtered, the filter cake washed with ether and the combined ether washings and dimethylformamide solution was concentrated in vacuo. The residue was partitioned between dilute sodium chloride solution and ether, and the ether solution was washed with 10% sodium hydroxide solution, water and 10% sodium chloride solution, dried over anhydrous sodium sulfate and concentrated in vacuo. The residue was distilled at 146°C. (0.02 mm.) to give 176.5 g. of ethyl 2-(4-acetyl-2-chlorophenoxy)-2-methylpropionate.

b. 2-(4-Acetyl-2-chlorophenoxy)-2-methylpropionic acid

A mixture of 10 g. of ethyl 2-(4-acetyl-2-chlorophenoxy)-2-methylpropinate, 15 ml. of 35% aqueous sodium hydroxide, 25 ml. of 95% ethanol and 100 ml. of water was stirred for 15 minutes. The mixture was then acidified with hydrochloric acid, cooled, and the solid product collected and recrystallized from aqueous ethanol to give 8.35 g. of 2-(4-acetyl-2-chlorophenoxy)-2-methylpropionic acid, m.p. 123°–125°C.

c. Ethyl 2-[4-(1-hydroxyethyl)-2-chlorophenoxy]-2-methylpropionate was prepared from 28.4 g. of ethyl 2-(4-acetyl-2-chlorophenoxy)-2-methylpropionate and 1.9 g. of sodium borohydride according to the procedure described above in Example 11, part (c). There was thus obtained 30.0 g. of ethyl 2-[4-(1-hydroxyethyl)-2-chlorophenoxy]-2 -methylpropionate.

d. Ethyl 2-(4-vinyl-2-chlorophenoxy)-2-methylpropionate was prepared from 28.6 g. of ethyl 2-[4-(1-hydroxyethyl)-2-chlorophenoxy]-2-methylpropionate and a trace of p-toluenesulfonic acid in 150 ml. of toluene according to the procedure described above in Example 11, part (d). The product was distilled at 110°–114°C. (0.05 mm.) to give 12.96 g. of ethyl 2-(4-vinyl-2-chlorophenoxy)-2-methylpropionate.

e. Ethyl 2-[2-chloro-4-(2,2-dichlorocyclopropyl)-phenoxy]-2-methylpropionate [I; A and A′ are $CH_3$, R is $C_2H_5$, $R^1$, $R^3$ and $R^{3'}$ are H, Q is 2-Cl, $R^2$ and $R^{2'}$ are Cl, and $n$ is O; para orientation] was prepared from 26.8 g. of ethyl 2-(4-vinyl-2-chlorophenoxy)-2-methylpropionate, 28 g. of potassium t-butoxide and 50 ml. of chloroform in 500 ml. of pentane according to the procedure described above in Example 1, part (b). The product was distilled at 135°–137°C. (0.08 mm.) to give 19.22 g. of ethyl 2-[2-chloro-4-(2,2-dichlorocyclopropyl)phenoxy]-2-methylpropionate.

EXAMPLE 13

Ethyl 2-[2-chloro-4-(2,2-difluorocyclopropyl)-phenoxy]-2-methylpropionate [I; A and A′ are $CH_3$, R is $C_2H_5$, $R^1$, $R^3$ and $R^{3'}$ are H, Q is 2-Cl, $R^2$ and $R^{2'}$ are F, and n is O; para orientation] was prepared from 40.3 g. of ethyl 2-(4-vinyl-2-chlorophenoxy)-2-methylpropionate and 32.9 g. of sodium chlorodifluoroacetate in 190 ml. of diglyme according to the procedure described above in Example 2, part (a). The product was distilled at 112°–114°C. (0.01 mm.) to give 26.39 g. of ethyl 2-[2-chloro-4-(2,2-difluorocyclopropyl)phenoxy]-2-methylpropionate.

EXAMPLE 14 a. Ethyl 2-(3-acetylphenoxy)-2-methylpropionate was prepared from 177 g. of m-hydroxyacetophenone, 632 g. of ethyl 2-bromo-2-methylpropionate, 537 g. of anhydrous potassium carbonate and 1200 ml. of dimethylformamide according to the procedure described above in Example 12, part (a). The product was distilled at 121°–128.5°C. (0.04 mm.) to give 227.3 g. of ethyl 2-(3-acetylphenoxy)-2-methylpropionate.

b. Ethyl 2-[3-(1-hydroxyethyl)phenoxy]-2-methylpropionate was prepared from 125 g. of ethyl 2-(3-acetylphenoxy)-2-methylpropionate and 9.45 g. of sodium borohydride according to the procedure described above in Example 11, part (c), affording 125.6 g. of ethyl 2-[3-(1-hydroxyethyl)phenoxy]-2-methylpropionate as an oil.

c. Ethyl 2-(3-vinylphenoxy)-2-methylpropionate was prepared from 125.6 g. of ethyl 2-[3-(1-hydroxyethyl)phenoxy]-2-methylpropionate and 4.5 g. of p-toluenesulfonic acid in 1500 ml. of toluene according to the procedure described above in Example 11, part (d), affording 115.9 g. of ethyl 2-(3-vinylphenoxy)-2-methylpropionate as an oil.

d. 2-[m-(2,2-Dichlorocyclopropyl)phenoxy]-2-methylpropionic acid [I; A and A′ are $CH_3$, R, $R^1$, $R^3$, $R^{3'}$ and Q are H, $R^2$ and $R^{2'}$ are Cl, and $n$ is O; meta orientation] was prepared from 35.1 g. of ethyl 2-(3-vinylphenoxy)-2-methylpropionate, 42.0 g. of potassium t-butoxide, 107 g. of chloroform and 750 ml. of pentane according to the procedure described above in Example 1, part (b). The product was distilled at 123°–125°C. (0.08 mm.) and chromatographed on a column of 500 g. of silica gel. The column was eluted with pentane and with pentane-ether mixtures and the resulting purified ethyl 2-[m-(2,2-dichlorocyclopropyl)phenoxy]-2-methylpropionate was hydrolyzed with 10 ml. of 35% sodium hydroxide solution in 100 ml. of 95% ethanol. After 20 minutes at room temperature, the reaction mixture was diluted and acidified and the acidified solution extracted with ether. The ether solution was concentrated in vacuo and the residue crystallized from hexane to give 8.77 g. of 2-[m-(2,2-dichlorocyclopropyl)phenoxy]-2-methylpropionic acid, m.p. 84°–86°C.

EXAMPLE 15 a. 2-(p-Acetylphenoxy)-2-methylpropionic acid was prepared from 545 g. of p-hydroxyacetophenone, 960 g. of sodium hydroxide and 715 g. of chloroform in 11 liters of acetone according to the procedure described above in Example 1, part (d). The product was recrystallized from carbon tetrachloride and from isopropyl acetate to give 2-(p-acetylphenoxy)-2-methylpropionic acid as a pale cream solid, m.p. 108°–110°C.

b. Ethyl 2-[p-(1-hydroxyethyl)phenoxy]-2-methylpropionate was prepared from 141 g. of ethyl 2-(p-acetylphenoxy)-2-methylpropionate [prepared by esterification of the acid of part (a) in a manner analogous to the procedure of Example 18, part (a)] and 10.7 g. of sodium borohydride according to the procedure described above in Example 11, part (c), affording 140 g. of ethyl 2-[p-(1-hydroxyethyl)phenoxy]-2-methylpropionate as a pale yellow liquid.

c. Ethyl 2-(p-vinylphenoxy)-2-methylpropionate.

A mixture of 116 g. of ethyl 2-[4-(1-hydroxyethyl)-phenoxy]-2-methylpropionate and 92 g. of p-toluenesulfonyl chloride in 500 ml. of pyridine was heated at reflux for three hours, kept at room temperature for about 16 hours and then heated at reflux again for six hours. The reaction mixture was poured into ice water and extracted with hexane. The hexane solution was washed successively with dilute sulfuric acid, 10% potassium bicarbonate, water and saturated sodium chloride solution, then dried over anhydrous magnesium sulfate and concentrated in vacuo. The residue was distilled at 104°–111°C. (0.03–0.08 mm.) to give 60 g. of ethyl 2-(p-vinylphenoxy)-2-methylpropionate.

d. Ethyl 2-[p-(2,2-dibromocyclopropyl)phenoxy]-2-methylpropionate was prepared from 23.4 g. of ethyl 2-(p-vinylphenoxy)-2-methylpropionate, 39.2 g. of potassium t-butoxide and 198 g. of bromoform according to the procedure described above in Example 1, part (b). The product was isolated and hydrolyzed without further purification.

e. 2-[p-(2,2-Dibromocyclopropyl)phenoxy]-2-methylpropionic acid [I; A and A' are $CH_3$, R, $R^1$, $R^3$, $R^{3'}$ and Q are H, $R^2$ and $R^{2'}$ are Br, and n is O; para orientation] was hydrolyzed with sodium hydroxide in aqueous ethanol, five hours at room temperature. The acid fraction was isolated and recrystallized from aqueous ethanol and from benzene-hexane 1:2 to give 18 g. of 2-[p-(2,2-dibromocyclopropyl)phenoxy]-2-methylpropionic acid, m.p. 129°–131°C.

EXAMPLE 16 a. Ethyl 2-[p-(2-chloro-2-fluorocyclopropyl)phenoxy]-2-methylpropionate.

A mixture of 13.6 g. of ethyl 2-(4-vinylphenoxy)-2-methylpropionate and 33 g. of phenyl dichlorofluoromethylmercury ($C_6H_5MgCCl_2F$) in 120 ml. of benzene was refluxed for 48 hours. The reaction mixture was allowed to stand at room temperature for two hours, then filtered and the filtrate evaporated in vacuo. The residue was mixed with pentane, filtered and concentrated in vacuo to give ethyl 2-[p-(2-chloro-2-fluorocyclopropyl)phenoxy]-2-methylpropionate as an orange oil which was hydrolyzed as described below.

b. 2-[p-(2-Chloro-2-fluorocyclopropyl)phenoxy]-2-methylpropionic acid [I; A and A' are $CH_3$, R, $R^1$, $R^3$, $R^{3'}$ and Q are H, $R^2$ is Cl m $R^{2'}$ is F, and n is O; para orientation] was prepared by hydrolysis of ethyl 2-[p-(2-chloro-2-fluorocyclopropyl)phenoxy]-2-methylpropionate in an aqueous ethanol solution of sodium hydroxide. There was thus obtained 14.4 g. of 2-[p-(2-chloro-2-fluorocyclopropyl)phenoxy]-2-methylpropionic acid in the form of beige needles, m.p. 97°–102°C. when recrystallized from a benzene-hexane mixture.

EXAMPLE 17 a. Ethyl 2-(p-phenylacetylphenoxy)-2-methylpropionate was prepared from 100 g. of p-phenylacetylphenol, 230 g. of ethyl 2-bromo-2methylpropionate and 228 g. of potassium carbonate according to the procedure described above in Example 12, part (a). There was thus obtained 70 g. of ethyl 2-(p-phenylacetylphenoxy)-2-methylpropionate, m.p. 110°–113°C.

b. Ethyl 2-[p-(1-hydroxy-2-phenethyl)phenoxy]-2-methylpropionate was prepared from 101 g. of ethyl 2-(p-phenylacetylphenoxy)-2-methylpropionate and 11.4 g. of sodium borohydride, affording 97.8 g. of ethyl 2-[p-(1-hydroxy-2-phenethyl)phenoxy]-2-methylpropionate as a yellow oil.

c. Ethyl 2-[p-(2-phenylvinyl)phenoxy]-2-methylpropionate was prepared from 94.5 g. of ethyl 2-[p-(1-hydroxy-2-phenethyl)phenoxy]-2-methylpropionate and 1.3 g. of p-toluenesulfonic acid in toluene according to the procedure described above in Example 11, part (d). The product was recrystallized from 95% ethanol to give 53.5 g. of ethyl 2-[p-(2-phenylvinyl)phenoxy]-2-methylpropionate, m.p. 55°–65°C.

d. Ethyl 2-[p-(2,2-dichloro-3-phenylcyclopropyl)phenoxy]-2methylpropionate.

A mixture of 25 g. of ethyl 2-[p-(2-phenylvinyl)phenoxy]-2-methylpropionate and 39 g. of phenyl dichlorobromomethylmercury in 100 ml. of benzene was heated at gentle reflux for three hours. An additional 5 g. of phenyl dichlorobromomethylmercury was then added and the mixture heated at reflux for three hours longer. The reaction mixture was kept at room temperature for two days, then filtered and the filtrate evaporated in vacuo. The residue was taken up in hexane, filtered and concentrated in vacuo to give 34.2 g. of ethyl 2-[p-(2,2-dichloro-3-phenylcyclopropyl)phenoxy]-2-methylpropionate as a brown oil which was hydrolyzed without further purification.

e. 2-[p-(2,2-Dichloro-3-phenylcyclopropyl)phenoxy]-2-methylpropionic acid [I; A and A' are $CH_3$, R, $R^1$, $R^{3'}$ and Q are H, $R^3$ is $C_6H_5$, $R^2$ and $R^{2'}$ are Cl, and n is O; para orientation] was prepared by hydrolyzing ethyl 2-[p-(2,2-dichloro-3-phenylcyclopropyl)phenoxy]-2-methylpropionate with aqueous ethanolic sodium hydroxide. The product was chromatographed twice on a column of silica gel and eluted with pentane-ether 1:1, and the product then recrystallized from hexane-benzene 2:1 to give 15 g. of 2-]p-(2,2-dichloro-3-phenylcyclopropyl)phenoxy]-2-methylpropionic acid, m.p. 129°–132°C.

METHOD C

EXAMPLE 18 a. Methyl 2-(p-acetylphenoxy)-2-methylpropionate was prepared by esterification of 222 g. of 2-(p-acetylphenoxy)-2-methylpropionic acid [Example 15, part (a)] by heating said acid with 96 g. of methanol and 7 ml. of concentrated sulfuric acid in 300 ml. of chloroform. The product was isolated and distilled at 114°C. (0.06 mm.) to give 206.6 g. of methyl 2-(p-acetylphenoxy)-2-methylpropionate, m.p. 62°–63°C.

b. Methyl 2-[p-(1,2-dimethylvinyl)phenoxy]-2-methylpropionate.

Sodium hydride (15.1 g., 0.36 mole, 57% in oil dispersion) was placed in a 2-liter flask and rinsed three times with pentane to remove the oil. Anhydrous dimethylsulfoxide (240 ml.) was then added, and the flask was evacuated and flushed with nitrogen. The mixture was heated to 75°–80°C. for 45 minutes, then cooled in an ice bath. A solution of 133.2 g. of ethyltriphenylphosphonium bromide in 720 ml. of dimethylsulfoxide was then added, the mixture stirred for 15 minutes and then treated with a solution of 70.8 g. (0.30 mole) of methyl 2-(p-acetylphenoxy)-2-methylpropionate in 120 ml. of dimethylsulfoxide. The reaction mixture was stirred for three hours at room temperature and then poured into water. The organic layer was separated, washed with water and saturated sodium chloride solution and dried over anhydrous sodium sulfate to give 81.8 g. of methyl 2-[p-(1,2-dimethylvinyl)phenoxy]-2-methylpropionate as an oil (mixture of geometric isomers). c. 2-[p-(2,2-Dichloro-1,3-dimethylcyclopropyl)phenoxy]-2-methylpropionic acid [I; A, A', $R^1$ and $R^3$ are $CH_3$, R, $R^{3'}$ and Q are H, $R^2$ and $R^{2'}$ are Cl, and n is 0; para orientation] was prepared from 24.8 g. of methyl 2-[p-(1,2-dimethylvinyl)phenoxy]-2-methylpropionate, 28 g. of potassium t-butoxide and 50 ml. of chloroform in 500 ml. of pentane according to the procedure described above in Example 1, part (b). The methyl ester thus obtained was hydrolyzed in the usual manner with sodium hydroxide in 95% methanol. The acid fraction thus obtained was recrystallized from a benzene-hexane mixture to give 12.5 g. of 2-[p-(2,2-dichloro-1,3-dimethylcyclopropyl)phenoxy]-2-methylpropionic acid, m.p. 138°-145°C. (mixture of geometric isomers).

EXAMPLE 19

2-[p-(2,2-Dibromo-1,3-dimethylcyclopropyl)phenoxy]-2-methylpropionic acid [I; A, A', $R^1$ and $R^3$ are $CH_3$, R, $R^{3'}$ and Q are H, $R^2$ and $R^{2'}$ are Br, and n is 0; para orientation] was prepared from 24.8 g. of methyl 2-[p-(1,2-dimethylvinyl)phenoxy]-2-methylpropionate, 35 g. of potassium t-butoxide and 152 g. of bromoform in 500 ml. of pentane according to the procedure described above in Example 1, part (b). The methyl ester thus obtained was hydrolyzed in the usual manner with sodium hydroxide in 95% ethanol, and the acid product was isolated and recrystallized from a benzene-hexane mixture to give 12.9 g. of 2-[p-(2,2-dibromo-1,3-dimethylcyclopropyl)phenoxy]-2-methylpropionic acid in the form of light tan rosettes, m.p. 141°-142.5°C. (decomp.) (greater than 90% trans-isomer).

EXAMPLE 20 a. Ethyl 2-(p-benzoylphenoxy)-2-methylpropionate was prepared from 198 g. of p-hydroxybenzophenone, 490 g. of ethyl 2-bromo-2-methylpropionate and 485 g. of potassium carbonate according to the procedure described above in Example 12, part (a). The neutral fraction was isolated and the resulting 208 g. of beige solid was recrystallized from a benzene-hexane mixture to give 180 g. of ethyl 2-(p-benzoylphenoxy)-2-methylpropionate, m.p. 82°-85°C.

b. Ethyl 2-[p-(1-phenylvinyl)phenoxy]-2-methylpropionate was prepared from 31.2 g. of ethyl 2-(p-benzoylphenoxy)-2-methylpropionate, 42.8 g. of methyltriphenylphosphonium bromide and 5.05 g. of sodium hydride in dimethylsulfoxide according to the procedure described above in Example 18, part (b), affording 31.6 g. of ethyl 2-[p-(1-phenylvinyl)phenoxy]-2-methylpropionate as a yellow liquid.

c. 2-[p-(2,2-Dichloro-1-phenylcyclopropyl)phenoxy]-2-methylpropionic acid [I; A and A' are $CH_3$, $R^1$ is $C_6H_5$, R, $R^3$, $R^{3'}$ and Q are H, $R^2$ and $R^{2'}$ are Cl, and n is 0; para orientation] was prepared from 31.6 g. of ethyl 2-[p-phenylvinyl)phenoxy]-2-methylpropionate, 28 g. of potassium t-butoxide and 50 ml. of chloroform according to the procedure described above in Example 1, part (b). The resulting ethyl ester was hydrolyzed in the usual manner with sodium hydroxide in 95% ethanol, and the acid product was isolated and recrystallized from a benzene-hexane mixture to give 20 g. of 2-[p-(2,2-dichloro-1-phenylcyclopropyl)phenoxy]-2-methylpropionic acid in the form of colorless needles, m.p. 171°-173°C.

EXAMPLE 21

2-[p-(2,2-Dibromo-1-phenylcyclopropyl)phenoxy]-2-methylpropionic acid [I; A and A' are $CH_3$, $R^1$ is $C_6H_5$, R, $R^3$, $R^{3'}$ and Q are H, $R^2$ and $R^{2'}$ are Br, and n is 0; para orientation] was prepared from 31.0 g. of ethyl 2-[p-(1-phenylvinyl)phenoxy]-2-methylpropionate [Example 20, part (b)], 35 g. of potassium t-butoxide and 152 g. of bromoform according to the procedure described in Example 1, part (b). The resulting ethyl ester was hydrolyzed in the usual manner with sodium hydroxide in 95% ethanol and the acid product was isolated and recrystallized several times from a benzene-hexane mixture to give 11.5 g. of 2-[p-(2,2-dibromo-1-phenylcyclopropyl)phenoxy]-2-methylpropionic acid in the form of colorless needles, m.p. 176°-178°C. (with gas evolution).

EXAMPLE 22

2-[p-(2,2-Difluoro-1-phenylcyclopropyl)phenoxy]-2-methylpropionic acid [I; A and A' are $CH_3$, $R^1$ is $C_6H_5$, R, $R^3$, $R^{3'}$ and Q are H, $R^2$ and $R^{2'}$ are F, and n is 0; para orientation] was prepared from 62 g. of ethyl 2-[p-(1-phenylvinyl)phenoxy]-2-methylpropionate [Example 20, part (b)] and 80 g. of sodium chlorodifluoroacetate in diglyme according to the procedure described above in Example 2, part (a). The resulting ethyl ester was hydrolyzed in the usual manner with sodium hydroxide in 95% ethanol, and the resulting acid product was recrystallized from a benzene-hexane mixture to give 31.3 g. of 2-[p-(2,2-difluoro-1-phenylcyclopropyl)phenoxy]-2-methylpropionic acid, m.p. 97°-99°C.

EXAMPLE 23 a. Methyl 2-[p-(1-ethylvinyl)phenoxy]-2-methylpropionate was prepared from 52.5 g. of methyl 2-(p-propionylphenoxy)-2-methylpropionate [Example 11, part (b)], 107 g. of methyltriphenylphosphonium bromide and 12.6 g. of sodium hydride in dimethylsulfoxide according to the procedure described above in Example 18, part (b). The product was distilled at 93°-95°C. (0.1 mm.) to give 37.5 g. of methyl 2-[p-(1-ethylvinyl)phenoxy]-2-methylpropionate.

b. Methyl 2-[p-(2,2-dichloro-1-ethylcyclopropyl)phenoxy]-2-methylpropionate [I; A, A' and R are $CH_3$, $R^1$ is $C_2H_5$, $R^3$, $R^{3'}$ and Q are H, $R^2$ and $R^{2'}$ are Cl, and n is 0; para orientation] was prepared from 18.5 g. of methyl 2-[p-(1-ethylvinyl)phenoxy]-2-methylpropionate, 21 g. of potassium t-butoxide and 56 g. of chloroform according to the procedure described above in Example 1, part (b), and was obtained in the form of a pale straw-colored oil, b.p. 131°-133°C. (0.09 mm.) (18.5 g.).

By the procedures described above, 3-methyl-4-hydroxyacetophenone reacts with ethyl 2-bromo-2-methylpropionate in the presence of potassium carbonate to form ethyl 2-(2-methyl-4-acetylphenoxy)-2-methylpropionate. The latter when treated with methyltriphenylphosphonium bromide in the presence of sodium hydride produces ethyl 2-[2-methyl-4-(1-methylvinyl)phenoxy]-2-methylpropionate, which then can be treated with chloroform in the presence of potassium t-butoxide to afford ethyl 2-[2-methyl-4-(2,2-dichloro-1-methylcyclopropyl)phenoxy]-2-methylpropionate [I; A, A', $R^1$ and Q are $CH_3$, R is $C_2H_5$, $R^3$ and $R^{3'}$ are H, $R^2$ and $R^{2'}$ are Cl, and n is 0; 2,4-orientation].

METHOD D

EXAMPLE 24 a. p-(2,2-Dichlorocyclopropyl)phenol.

A solution of 50 g. (0.248 mole) of p-(2,2-dichlorocyclopropyl)aniline in 185 ml. of glacial acetic acid was cooled to about 10°C., and a solution of 18.9 g. (0.273 mole) of sodium nitrite in 185 ml. of water was added dropwise to the stirred solution. A thick slurry formed and this was added portionwise to a stirred solution of 160 ml. of concentrated sulfuric acid in 320 ml. of water held at 100°–105°C. The reaction mixture was stirred at 100 ± 5°C. for 10 minutes, then cooled and diluted with water. The resulting product was collected by filtration, dissolved in ether and washed with sodium bicarbonate solution. The ether solution was then extracted with sodium hydroxide solution, and the sodium hydroxide solution was acidified and extracted with ether. The ether solution was dried and concentrated in vacuo, and the residue (18 g.) was steam distilled affording 9 g. of a yellow gum which crystallized when triturated with ether. There was thus obtained 8 g. of p-(2,2-dichlorocyclopropyl)-phenol, m.p. 54.5°–56°C.

b.
2-[p-(2,2-Dichlorocyclopropyl)phenoxy]-2-methyl-propionic acid

[I; A and A' are $CH_3$, R, $R^1$, $R^3$, $R^{3'}$ and Q are H, $R^2$ and $R^{2'}$ are Cl, and $n$ is 0; para orientation].

A mixture of 8 g. (0.0356 mole) of p-(2,2-dichlorocyclopropyl)phenol, 11.2 g. (0.28 mole) of sodium hydroxide pellets, 11 g. of chloroform and 350 ml. of acetone was prepared at 0°C. The cooling bath was removed, the mixture stirred for a minute and then heated on a steam bath to reflux temperature. The reaction mixture was stirred at reflux for three hours and then concentrated in vacuo. The residual gum was partitioned between dilute hydrochloric acid and ether, and the ether layer was separated, dried and concentrated in vacuo. The residual oil (14 g.) was partitioned between dilute aqueous sodium bicarbonate and ether. The sodium bicarbonate solution was acidified with concentrated hydrochloric acid and extracted with ether. The ether solution was dried over anhydrous sodium sulfate and concentrated. The residue (9.5 g. of yellow oil) was crystallized twice from hexane to give 6.0 g. of 2-[p-(2,2-dichlorocyclopropyl)phenoxy]-2-methylpropionic acid in the form of a pale cream-colored solid, m.p. 114°–116°C.

EXAMPLE 25

Methyl 2-[p-(2,2-dichlorocyclopropyl)phenoxy]-2-methylpropionate

[I; A, A' and R are $CH_3$, $R^1$, $R^3$, $R^{3'}$ and Q are H, $R^2$ and $R^{2'}$ are Cl, and $n$ is 0; para orientation].

A mixture of 10 g. (0.0346 mole) of 2-[p-(2,2-dichlorocyclopropyl)phenoxy]-2-methylpropionic acid [Example 24, part (b)], 3.33 g. (0.1038 mole) of methanol and 0.5 ml. of concentrated sulfuric acid in 100 ml. of methylene dichloride was stirred at reflux for four hours. The reaction mixture was cooled, washed with water and sodium bicarbonate solution, dried and concentrated in vacuo. The residue was distilled to give 8.5 g. of methyl 2-[p-(2,2-dichlorocyclopropyl)-phenoxy]-2-methylpropionate as a colorless oil, b.p. 115°C. (0.05 mm.).

Alternatively, methyl 2-[p-(2,2-dichlorocyclopropyl)phenoxy]-2-methylpropionate was prepared from 20 g. of p-(2,2-dichlorocyclopropyl)phenol [Example 24, part (a)], 38 g. of ethyl 2-bromo-2-methylpropionate and 42 g. of potassium carbonate in 100 ml. of acetonitrile. The ethyl 2-bromo-2-methylpropionate was added in two equal portions, the second portion being added after seven hours of heating at reflux. The reaction mixture was heated at reflux for about three days and the product isolated to give 32 g. of ethyl 2-[p-(2,2-dichlorocyclopropyl)phenoxy]-2-methylpropionate. The latter was hydrolyzed in the usual manner with ethanolic sodium hydroxide to produce 2-[p-(2,2-dichlorocyclopropyl)phenoxy]-2-methylpropionic acid, identical with the compound formed in Example 24, part (b).

By replacing the ethyl 2-bromo-2-methylpropionate in the foregoing alternative preparation by a molar equivalent amount of methyl 2-bromo-2-(n-propyl)valerate, methyl 2-bromo-2-ethylbutyrate, methyl 2-bromo-2-methylbutyrate or methyl 2-bromo-2,3-dimethylbutyrate there can be obtained, respectively, methyl 2-[p-(2,2-dichlorocyclopropyl)phenoxy]-2-(n-propyl)valerate [I; A and A' are $CH_2CH_2CH_3$, R is $CH_3$, $R^1$, $R^3$, $R^{3'}$ and Q are H, $R^2$ and $R^{2'}$ are Cl, and $n$ is 0; para orientation]; methyl 2-[p-(2,2-dichlorocyclopropyl)phenoxy]-2-ethylbutyrate [I; A and A' are $C_2H_5$, R is $CH_3$, $R^1$, $R^3$, $R^{3'}$ and Q are H, $R^2$ and $R^{2'}$ are Cl, and $n$ is 0; para orientation]; methyl 2-[p-(2,2-dichlorocyclopropyl)phenoxy]-2-methylbutyrate [I; A and R are $CH_3$, A' is $C_2H_5$, $R^1$, $R^3$, $R^{3'}$ and Q are H, $R^2$ and $R^{2'}$ are Cl, and $n$ is 0; para orientation]; or methyl 2-[p-(2,2-dichlorocyclopropyl)phenoxy]-2,3-dimethylbutyrate [I; A and R are $CH_3$, A' is $CH(CH_3)_2$, $R^1$, $R^3$, $R^{3'}$ and Q are H, $R^2$ and $R^{2'}$ are Cl, and $n$ is 0; para orientation].

I claim:
1. A compound of the formula wherein:
R is hydrogen or alkyl of 1–6 carbon atoms;
A and A' are alkyl of 1–3 carbon atoms;
Q is hydrogen, halogen or alkyl of 1–3 carbon atoms;
$R^1$ is hydrogen, alkyl of 1–3 carbon atoms or phenyl;
$R^2$ is hydrogen or halogen;
$R^{2'}$ is hydrogen or halogen, at least one of $R^{2'}$ and $R^2$ being halogen;
$R^3$ is hydrogen, alkyl of 1–3 carbon atoms or phenyl;
$R^{3'}$ is hydrogen or alkyl of 1–3 carbon atoms;
$n$ is 0 or 1;
a compound of the above formula where Q and $R^3$ together form an ethylene bridge and $(CH_2)_n$ is a single bond to the benzene ring ortho to Q, thereby forming the six-membered non-aromatic carbocyclic ring of a 2,3-dihydro-1H-cyclopropa[a]-naphthalene ring system;
or a pharmacologically acceptable salt of a compound of the above formula where R is hydrogen.
2. A compound according to claim 1 in which $R^2$ and $R^{2'}$ are both halogen, A and A' are methyl, Q is hydrogen and $n$ is 0.

3. 2-[p-(2,2-Dichlorocyclopropyl)phenoxy]-2-methylpropionic acid, according to claim 2.

4. 2-[p-(2,2-Difluorocyclopropyl)phenoxy]-2-methylpropionic acid, according to claim 2.

5. 2-[p-(2,2-Dichloro-1-methylcyclopropyl)phenoxy]-2-methylpropionic acid, according to claim 2.

6. 2-[p-(2,2-Dibromocyclopropyl)phenoxy]-2-methylpropionic acid, according to claim 2.

7. 2-[p-(2-Chloro-2-fluorocyclopropyl)phenoxy]-2-methylpropionic acid, according to claim 2.

8. Ethyl 2-[2-chloro-4-(2,2-dichlorocyclopropyl)phenoxy]-2-methylpropionate, according to claim 1.

9. Ethyl 2-[2-chloro-4-(2,2-difluorocyclopropyl)phenoxy]-2-methylpropionate, according to claim 1.

10. 2-(1,1-Dichloro-2,3-dihydro-1H-cyclopropa[a]-5-naphthyloxy)-2-methylpropionic acid, according to claim 1.

11. 2-[p-(2,2-Dichlorocyclopropylmethyl)phenoxy]-2-methylpropionic acid, according to claim 1.

* * * * *